(12) United States Patent
Lattner (10) Patent No.: US 7,615,578 B2
(45) Date of Patent: Nov. 10, 2009

(54) FAST FLUID BED METHANOL SYNTHESIS

(75) Inventor: James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 302 days.

(21) Appl. No.: 11/801,436

(22) Filed: May 10, 2007

(65) Prior Publication Data

US 2007/0299146 A1    Dec. 27, 2007

Related U.S. Application Data

(60) Provisional application No. 60/816,406, filed on Jun. 26, 2006.

(51) Int. Cl.
C07C 27/00    (2006.01)
(52) U.S. Cl. .................. 518/713; 518/700; 518/714
(58) Field of Classification Search .............. 518/700, 518/713, 714
See application file for complete search history.

(56) References Cited

U.S. PATENT DOCUMENTS

| | | |
|---|---|---|
| 4,956,392 A | 9/1990 | Saito et al. |
| 5,216,034 A | 6/1993 | Sie |
| 5,512,599 A | 4/1996 | Hiramatsu et al. |
| 2005/0197412 A1 | 9/2005 | Van Egmond et al. |

FOREIGN PATENT DOCUMENTS

GB    2 202 531    9/1988

OTHER PUBLICATIONS

Modern Production Technologies, British Sulphur Publishing, London, 1997, Chapter 3—Methanol, pp. 69-101, ISBN 1 873387 26 1.
Rodney J. Dry, Possibilities for the Development of Large-Capacity Methanol Synthesis Reactors for Synfuel Production, Ind. Eng. Chem. Res., 1988, vol. 27, pp. 616-624.
H.Scott Fogler, Elements of Chemical Reaction Engineering, 2nd ed., Prentice Hall, London, 1992, p. 38-48.

*Primary Examiner*—Jafar Parsa
(74) *Attorney, Agent, or Firm*—Kevin M. Faulkner; David M. Weisberg (57) ABSTRACT

This invention is directed to a process for making a methanol product from a synthesis gas (syngas) feed using a fast fluid bed reactor. The reactor is operated at substantially plug flow type behavior. The heat from circulated catalyst is sufficient to initiate the reaction process with little to no preheating of feed required. In addition, little if any internal reactor cooling is needed.

26 Claims, 2 Drawing Sheets

FAST FLUID BED METHANOL SYNTHESIS

CROSS REFERENCE TO RELATED APPLICATIONS

This claims the benefit of and priority from U.S. Ser. No. 60/816,406, filed Jun. 26, 2006. The above application is fully incorporated herein by reference.

FIELD OF THE INVENTION

This invention relates to the production of methanol. In particular, this invention relates to the production of methanol using a fast fluidized bed reactor.

BACKGROUND OF THE INVENTION

Current technology limits the size of a single train methanol plant to about 5000 t/day. There is incentive to increase the scale of methanol production to enable economic conversion of remote natural gas into a transportable form, either for fuel needs or for other processes such as methanol-to-olefins (MTO) processes. Such prospects may entail increasing methanol production on a scale of from 2 to 4 times current processes.

Many methanol synthesis reactor designs currently utilize some sort of external cooling that takes place as the reaction proceeds. See *Appl, M., Modern Production Technologies*, British Sulphur Publishing, London, 1997 ISBN 1 8733387 26 1. Generally, the external cooling takes place in one of two ways: (i) several adiabatic reactor beds in series with coolers in between stages, or (ii) cooling tubes located within the fixed reactor bed. Either of these methods results in a relatively complicated reactor design due to the need for integrated cooling. The reactor feed must be preheated, and then additional heat transfer surface is required to remove the heat of reaction.

U.S. Pat. No. 5,512,599 discloses an ultra-large scale reaction apparatus capable of producing 5,000 tons/day or more of methanol. The methanol can be synthesized by means of a fluidized bed reactor at a linear velocity of 0.51 m/sec. The fluidized bed catalytic reactor includes internal heat transfer tubes.

U.S. Pat. No. 5,216,034 discloses the use of multiple reactors in series for making methanol. The reactors include catalyst in a fluidized bed. Each reactor is equipped with at least one heat exchanger, an inlet for synthesis gas and an outlet for the reaction mixture. Each outlet is connected to a heat exchanger, which is connected to a gas/liquid (methanol) separator. The separator has an outlet for unconverted synthesis gas, and the outlet is connected to the next reactor in series.

U.S. Pat. No. 4,956,392 discloses a process for producing methanol. Synthesis gas feed is passed through a fluidized bed catalytic reactor at a superficial linear velocity of at heat 0.2 m/sec. Heat is recovered from the reaction by passing a heat transfer medium though a heat transmission tube in the reactor.

U.K. Patent No. GB 2 202 531 discloses a process for producing methanol or mixed alcohol from synthesis gas using a fluidized catalyst bed. Catalyst particles in the bed are contacted with the synthesis gas at a superficial linear velocity of at least 0.2 m/sec and a pressure of 40 to 200 atmospheres. A heat transmission tube is installed in the reactor.

What is needed is a reaction system that substantially reduces or eliminates the need for integrated heat transfer within the reaction zone. Such a system would be particularly beneficial if it were uncomplicated in design, had a relatively even temperature profile, and provided a high degree of plug flow like characteristics and/or a high degree of heat transfer. In addition, the system should be easily scaled to very large capacities.

SUMMARY OF THE INVENTION

This invention provides a process for producing methanol using a fluidized bed reactor, in particular, a fast fluidized bed reactor system. The reactor system is uncomplicated in design, provides a high degree of plug flow like characteristics and is highly efficient in transferring heat to initiate the reaction process. The reactor itself can be easily scaled to very large capacities.

According to one aspect of the invention, there is provided a process for making methanol product in a fluid bed reactor. The process comprises flowing a gas containing carbon monoxide and hydrogen through a fluidized bed zone of a fluid bed reactor at a superficial gas velocity of at least 2 meters per second. The gas is contacted with methanol synthesis catalyst in the fluidized bed zone to form the methanol product, and the fluidized bed zone is maintained at a solids volume fraction of from 0.05 to 0.35. Preferably. the catalyst is separated from the methanol product in an upper portion of the reactor. In one embodiment, the catalyst that is separated from the methanol product is returned to the fluidized bed.

In one embodiment of the invention, the fluidized zone is maintained at a solids volume fraction of from 0.07 to 0.3. Preferably the fluidized zone is maintained at a solids volume fraction of from 0.1 to 0.25.

In another embodiment of the invention, the reactor has an internal heat exchange surface area ($m^2$) relative to internal reactor volume ($m^3$) of not greater than 100 $m^2/m^3$. Preferably, the catalyst in the fluidized bed is maintained at a solids volume fraction of from 0.05 to 0.35.

In yet another embodiment, the reaction process includes one or more reactors with no two reactors in series.

Preferably, the catalyst has a particle size of from 20 to 300 microns. More preferably, the methanol synthesis catalyst includes an oxide of at least one element selected from the group consisting of copper, silver, zinc, boron, magnesium, aluminum, vanadium, chromium, manganese, gallium, palladium, osmium and zirconium.

In a particular embodiment, wherein the fluidized bed zone is maintained at a temperature of from 150° C. to 350° C. Preferably, the gas flows into the fluidized bed zone at a temperature of from 50° C. to 150° C.

In another embodiment, the feed gas further contains $CO_2$, and the gas is contacted with the catalyst at a rate to control molar conversion of the CO and $CO_2$, based on the total amount of CO and $CO_2$ in the feed, in a range of from 20% to 70%. In a further embodiment, at least a portion of the methanol product is contacted with an olefin forming catalyst to form an olefin product.

DETAILED DESCRIPTION OF THE INVENTION

I. Balance of Heat Transfer Using a Fluidized Bed

This invention is directed to a process for making a methanol product from a synthesis gas (syngas) feed using a fluid bed reactor, in particular a fast fluid bed (e.g., riser reactor, transport reactor). The reactor is operated in the gas phase, with catalyst particles being flowed along with the feed in the reactor, and is preferably operated at substantially plug flow type behavior. Catalyst and product are separated and the catalyst is circulated to the bottom of the reactor. The circulated catalyst retains heat from the exothermic reaction process, and this heated catalyst is again contacted with feed. The heat from the catalyst is sufficient to initiate the reaction process with little to no preheating of feed required. In addition, little if any internal reactor cooling is needed. Preferably, the reactor needs no internal cooling means.

The reactor used in the invention can be of any type of reactor in which a fast fluidized type bed can be maintained. Examples of such reactors are shown in *Fluidization Engineering*, D. Kunii and O. Levenspiel, Robert E. Krieger Publishing Company, New York, N.Y. 1977.

The fast fluidized bed regime can be characterized in one aspect by superficial gas velocity (SGV), which is defined as volumetric flow rate of gas leaving the reactor ($m^3$/sec) divided by the average cross sectional diameter of the reactor ($m^2$). In one embodiment, the reactor is operated at a superficial gas velocity of at least 2 meters per second, preferably at least 3 meters per second, more preferably at least 4 meters per second. Preferably, the reactor is maintained at a superficial gas velocity of from 2 to 20 meters per second, more preferably from 3 to 10 meters per second.

The fast fluidized regime can also be characterized by volume fraction. In one embodiment, a fast fluidized bed regime is characterized in that the fast fluidized zone is maintained at a particular solids volume fraction, and gas is contacted with catalyst in a fluidized bed zone of a reactor at the desired solids volume fraction. In one embodiment, feed gas us contacted with methanol synthesis catalyst in a fluidized bed zone of a reactor, with the fluidized bed zone being maintained at a solids volume fraction of from 0.05 to 0.35. This means that within the reactor (e.g., riser reactor portion) 5% to 35% of the volume is occupied by solid catalyst particles. Preferably, the catalyst in the fast fluidized zone is maintained at a solids volume fraction of from 0.07 to 0.3, more preferably from 0.1 to 0.25.

The catalyst in the reactor can be maintained in the fluidized state by injecting gas, e.g., the feed, into a lower portion of the reactor so as to move the catalyst along with the gas. Preferably, the feed gas is injected into a lower portion of the riser, where the catalyst contacts the feed and both move in an upward direction at the desired space velocity.

A particular benefit of using the fast fluid flow regime is that the amount of catalyst used in the reactor can be reduced relative to other reactors. In particular, the amount of catalyst in the fast fluidized reaction zone is typically less for a comparably sized dense fluid bed reactor. In a comparably sized tubular bed reactor, the amount of catalyst can be generally about the same, but there is a substantial advantage over the tubular bed reactor in that the tubular bed reactor requires substantial cooling. This means that tubular bed reactors typically require complex heat exchange systems and such systems are not required in a fast fluidized bed system.

At certain capacities, the particular benefits of the fast fluidized bed reaction system can be obtained when the feed gas is contacted with methanol synthesis catalyst in a fluidized bed zone portion of a fluid bed reactor, the fluidized bed portion of the reactor having one or more of: i) a reactor height to diameter ratio of at least 2, ii) a reactor diameter to reactor volume ratio ($m/m^3$) of less than 0.05, and iii) a reactor height to volume ratio ($m/m^3$) of greater than 1 so as to form methanol product. Preferably, the fluidized bed zone portion of the reactor has at least two of: i) a reactor height to diameter ratio of at least 2, ii) a reactor diameter to volume ratio ($m/m^3$) of greater than 0.1, and iii) a reactor height to volume ratio ($m/m^3$) of greater than 1. More preferably, the fluidized bed zone portion of the reactor has each of: i) a reactor height to diameter ratio of at least 2, ii) a reactor diameter to volume ratio ($m/m^3$) of greater than 0.1, and iii) a reactor height to volume ratio ($m/m^3$) of greater than 1.

In one embodiment, the fluidized bed zone portion of the reactor has a reactor height to diameter ratio of at least 2, preferably at least 5. More preferably, the fluidized bed zone portion of the reactor has a reactor height to diameter ratio of at least 10. In another embodiment, the fluidized bed zone portion of the reactor has a reactor height to diameter ratio of not greater than 500, preferably not greater than 200, and more preferably not greater than 100.

In another embodiment, the fluidized bed zone portion of the reactor has a reactor diameter to reactor volume ratio ($m/m^3$) of less than 0.04. Preferably, the fluidized bed zone portion of the reactor has a reactor diameter to reactor volume ratio ($m/m^3$) of less than 0.03. In another embodiment, the fluidized bed zone portion of the reactor has a reactor diameter to reactor volume ratio ($m/m^3$) of greater than 0.005, preferably greater than 0.01.

In another embodiment, the fluidized bed zone portion of the reactor has a reactor height to volume ratio ($m/m^3$) of greater than 1. Preferably, the fluidized bed zone portion of the reactor has a reactor height to volume ratio ($m/m^3$) of greater than 1.2, more preferably greater than 1.4.

The particle size of the catalyst can also contribute to the effective fluidization and backmixing of the catalyst. In one embodiment of the invention, the catalyst bed includes catalyst particles having a particle size (i.e., average diameter) of from 20 to 300 microns. Preferably, the catalyst particles have a particle size of from 40 to 200 microns.

The temperature in the fluidized bed zone itself can be controlled in numerous ways even though it is not necessary to incorporate heat transfer means within the reactor. For example, feed preheat, throughput or catalyst volume can be controlled to accomplish the desired objectives of conversion and overall temperature.

In one embodiment of the invention, the fluidized bed zone is maintained at a temperature of from 150° C. to 350° C. Preferably fluidized bed is maintained at a temperature of from 175° C. to 325° C., more preferably from 200° C. to 300° C.

In one embodiment, the temperature of the fluidized bed zone is maintained by controlling the feed gas entering the reactor. The temperature of the feed gas can be kept at an appropriate reactor inlet temperature as to limit the temperature within the reactor vessel. Preferably, the gas flowing through the fluidized bed zone of the fluid bed reactor flows into the zone at a temperature of from 50° C. to 150° C. More preferably the gas flows into the fluidized bed zone at a temperature of from 60° C. to 120° C., and most preferably from 70° C. to 100° C.

Since the reaction process is an exothermic process, the temperature within the fluidized bed zone can be controlled by limiting the conversion of the reactants. In one embodiment, the feed gas contains CO and $CO_2$, and the gas is contacted with the catalyst at a rate to control molar conversion of the CO and $CO_2$, based on the total amount of CO and $CO_2$ in the feed, in a range of from 20% to 70%. Preferably conversion of the CO and $CO_2$ is maintained in a range of from 30% to 60%, more preferably from 35% to 55%.

Because the reactor is maintained to balance the heat of the reaction with the amount of desired feed preheat, little if any internal reactor cooling is needed. In one embodiment, the reactor has an internal heat exchange surface area ($m^2$) relative to internal reactor volume ($m^3$) of not greater than 100 $m^2/m^3$. Preferably, the reactor has an internal heat exchange surface area ($m^2$) relative to internal reactor volume ($m^3$) of not greater than 50 $m^2/m^3$, more preferably not greater than 10 $m^2/m^3$.

The overall reaction process can include one or more reactors. Preferably, the process includes one or more reactors, with no two reactors in series.

The gas feed entering the fluidized bed reactor system is preferably converted, partially or fully, in the fast fluidized zone (e.g., riser portion) into a gaseous effluent. The gaseous effluent includes methanol product and generally some unreacted syngas components. Preferably, the gaseous effluent is sent to a disengaging zone or vessel so separate entrained catalyst from the gaseous components. In one embodiment, one or more cyclones are provided within the disengaging zone to separate the catalyst composition from the gaseous effluent. Preferably, the disengaging zone and cyclones are located in an upper portion of the disengaging zone. Other methods can also be used to separate the catalyst from the gaseous components. For example, gravity effects within the disengaging vessel can also be used to separate the catalyst composition from the gaseous effluent. Other methods for separating the catalyst composition from the gaseous effluent include the use of plates, caps, elbows, and the like. The catalyst disengaged from the gaseous effluent is returned to the fast fluidized bed reaction zone, and contacts syngas feed as it enters the fast fluidized bed reaction zone, preferably at a lower or bottom riser reactor portion of the fast fluidized bed reaction zone.

Figure 1:
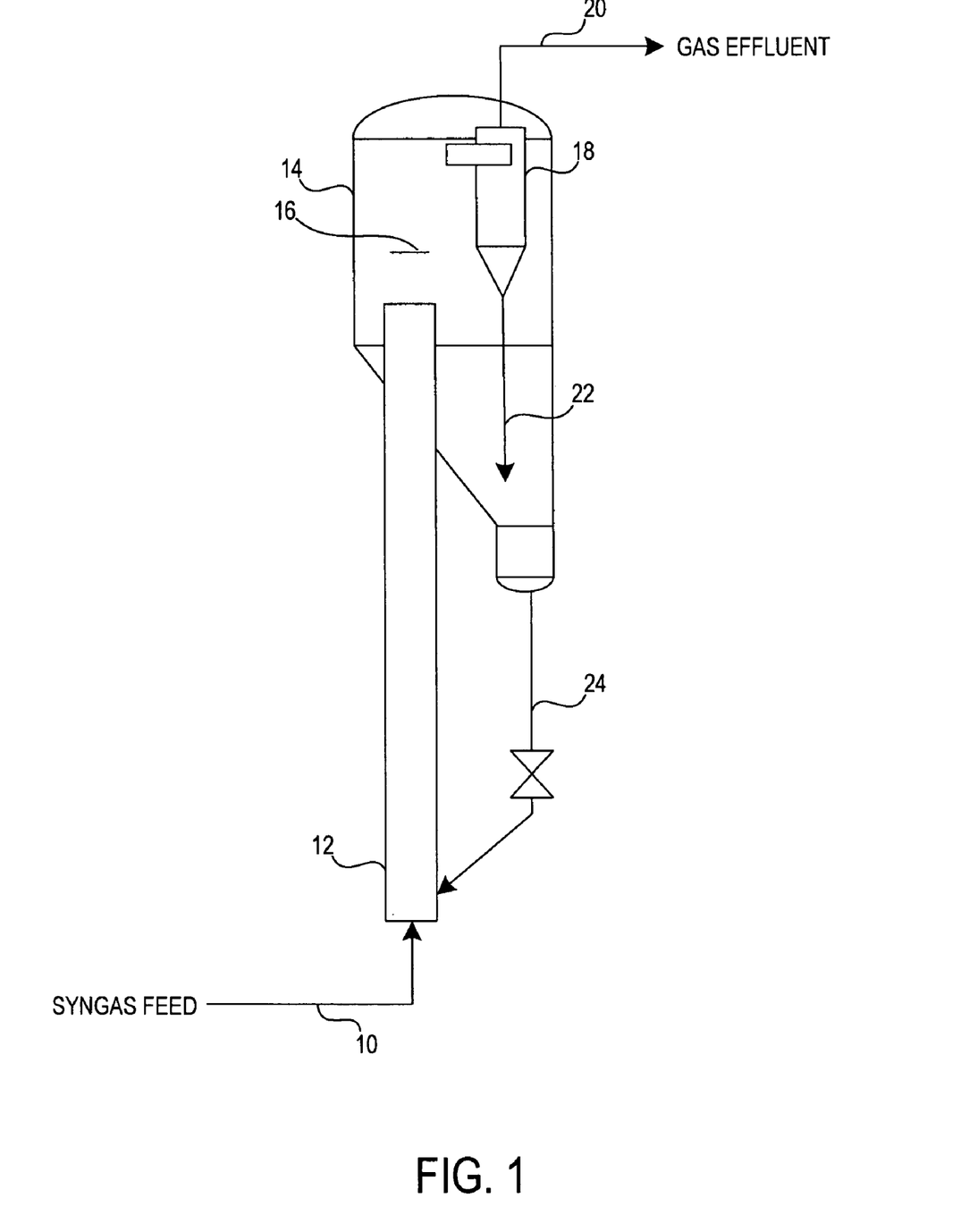
FIG. 1 is shows an example of a fast fluid bed reactor in which the reactor includes no internal cooling means or devices.

One example of a fast fluidized bed reactor that can be used in this invention is shown in the FIG. 1. According to this example, syngas feed is sent through a line 10 to a riser reactor 12. Catalyst from a line 24 is also sent to the riser reactor 12. In the riser reactor 12, the catalyst and feed contact one another and both are flowed in an upward direction through the riser reactor 12. It is in this riser reactor portion 12 that the flowing catalyst is referred to as being in a fast fluidized bed mode or zone, and is where a significant portion of the reaction of converting feed to methanol is carried out.

Gaseous effluent (e.g., reaction product, some unreacted feed and/or by-product) and catalyst leaves the riser reactor 12 and contacts an impingement plate 16 in a disengaging zone 14. This contact separates much of the catalyst from the gaseous effluent, sending the catalyst into a bottom portion of the disengaging zone 14. Gaseous effluent and some of the catalyst particles flow into a cyclone separation system 18, which separates the catalyst from the gaseous effluent. The gaseous effluent is removed from the disengaging zone 14 by way of a line 20, and catalyst is sent down a line 22 to the bottom portion of the disengaging zone 14. Catalyst from the disengaging zone 14 is then sent through a line 24 and back into riser 12. The catalyst flowing through line 24 maintains much of the heat generated during the reaction in riser 12, and this heat is used to initiate the reaction of new syngas feed entering the riser 12 and contacting the catalyst.

II. Synthesis Gas

The methanol manufacturing process of this invention uses synthesis gas (syngas) as feed. Synthesis gas comprises carbon monoxide and hydrogen. Optionally, carbon dioxide and nitrogen are included.

Synthesis gas can be manufactured from a variety of carbon or hydrocarbon sources. Examples of such sources include biomass, natural gas, $C_1$-$C_5$ hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

Although synthesis gas can be manufactured from a variety of carbon sources, a preferred embodiment of the invention uses natural gas feedstocks comprising methane. The transformation of hydrocarbons into syngas is an endothermic reaction, meaning that heat must be supplied to make the reaction proceed. There are generally two methods of adding heat: (i) indirect heating, generally by burning a fuel and transferring this heat across a metal membrane to the reaction zone, and (ii) in-situ heat generation by adding oxygen to the reformer feed, which results in exothermic oxidation reactions which supply heat for the endothermic. Steam is typically used in method (i), and this process is generally referred to as steam reforming. In method (ii), oxygen is typically added, and this process is generally referred to as oxygen-blown reforming. Various combinations of (i) and (ii) are possible, and are typically referred to as combined reforming.

Oxygen blown reforming can be operated with or without a catalyst. When no catalyst is used, the process is typically referred to as partial oxidation, or POX. The feedstock hydrocarbon and oxygen-containing gas are preheated and react in a burner. When catalyst is used, the oxygen-blown reforming can be further subdivided into two categories. If the feedstock hydrocarbon and oxygen-containing gas are pre-mixed, without reaction, before passing across a catalyst bed, the process is generally referred to as catalytic partial oxidation, or CPOX. When preheated feedstock and oxygen are combined in a burner, where exothermic reactions occur, before passing across a catalyst bed, the process is generally referred to as autothermal reforming, or ATR.

Steam reformers operated with natural gas feedstock produce syngas that is rich in hydrogen, with stoichiometric molar ratios ($S_N$) approaching 3.0. Oxygen-blown reformers produce syngas that is less rich in hydrogen, and generally have $S_N$ values below the theoretical required value for methanol of 2.0.

The amount of oxygen added to an oxygen-blown reformer depends upon the pressure, feed temperatures, feed compositions and diluent rates, and the desired level of conversion. The total molar flow rate of oxygen added to the reformer, divided by the flow rate of hydrocarbon-based carbon atoms fed to the reformer, will be referred to as the oxygen:carbon ratio.

Steam may be added to an oxygen-blown reformer, either as diluent to the hydrocarbon feedstock, diluent to the oxygen-containing gas, or may be directly injected into a specific portion of the reforming reactor to achieve localized cooling. The total molar flow rate of steam added to the oxygen-blown reformer in any manner, divided by the flow rate of hydrocarbon-based carbon atoms fed to the reformer, will be referred to as the steam:carbon ratio.

In the autothermal reforming of natural gas, steam is added to the feed as a means to reduce or eliminate soot formation, to cool select components of the burner within the ATR, and to reduce the methane content of the syngas at a given temperature. It is desirable to minimize the amount of steam added, so that less energy is required for generation of the steam, and so that the volume of gas passing through the reformer is minimized. ATR reactors generally require steam: carbon ratios of 1.2 to 2.0, although more recent technology allows operation in the 0.4 to 1.2 range. The oxygen:carbon ratio of an ATR ranges between 0.4 to 0.8, preferably between 0.5 and 0.6.

In the partial oxidation of natural gas, the formation of soot is less of a concern because there is no catalyst bed to become fouled or plugged by the soot. Therefore, POX reformers can run with very little or no steam, with steam:carbon ratios between 0 and 0.2. the oxygen:carbon ratio of POX reformers ranges between 0.4 to 0.8, preferably between 0.55 and 0.7.

The catalytic partial oxidation reforming process has not been commercialized to-date for methanol synthesis applications. A CPOX reforming process can theoretically operate with steam:carbon ratios below 0.2, or at any higher level of steam:carbon. A CPOX reformer will generally operate with an oxygen:carbon ratio between 0.4 and 0.8.

Any oxygen-blown reforming reactor will generally reach a product gas that approaches the most thermodynamically stable composition. One skilled in the art can calculate the adiabatic temperature and product syngas composition at thermodynamic equilibrium for any given feed composition, feed temperature, and pressure. The relative amounts of CO and $CO_2$ in the syngas is determined by the water gas shift (WGS) reaction equilibrium represented in equation (3) above.

Increasing the level of steam added to the reformer will shift the reaction to the right, resulting in a greater proportion of $CO_2$ relative to CO. Higher reaction temperatures shift the equilibrium of the WGS to the left, resulting in reduced proportions of $CO_2$ relative to CO. It is easily shown that the stoichiometric number for methanol, $S_N$, is not affected by shifting between CO and $CO_2$ due to the WGS reaction. The $CO_2$ content of the syngas, however, is affected by the WGS reaction. Low levels of $CO_2$ in the syngas are favored by low steam:carbon and high temperatures in the reformer.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process comprises a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminum titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

III. Syngas Feed to the Fluidized Bed Reactor

Synthesis gas (syngas) is used in the feed to the fluidized bed reaction system of this invention. Desirably, the synthesis gas feed (including any recycle syngas recovered from the process itself as well as fresh syngas) has a molar ratio of hydrogen ($H_2$) to carbon oxides ($CO+CO_2$) in the range of from about 0.5:1 to about 20:1, preferably in the range of from about 1:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas, and preferably less than 20% by weight, more preferably less than 10% by weight.

Desirably, the stoichiometric molar ratio is sufficiently high so as maintain a high yield of methanol, but not so high as to reduce the volume productivity of methanol. Preferably, the synthesis gas fed to the methanol synthesis process has a stoichiometric molar ratio (i.e., a molar ratio of ($H_2-CO_2$)/($CO+CO_2$)) of from about 1.0:1 to about 2.7:1, more preferably from about 1.5 to about 2.5, more preferably a stoichiometric molar ratio of from about 1.7:1 to about 2.5:1.

IV. Catalyst

Preferably, the methanol synthesis catalyst used in the process of this invention includes an oxide of at least one element selected from the group consisting of copper, silver, zinc, boron, magnesium, aluminum, vanadium, chromium, manganese, gallium, palladium, osmium and zirconium. More preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

V. Recovery and Further Processing of Methanol Product

The methanol product from the fluidized bed reactor is generally sent to a separation unit or vessel to remove light product having a higher boiling point than the methanol. This separation preferably yields a liquid product rich in methanol, although the separated methanol product can include other components such as water. The separated methanol product can be used "as is," or it can be further processed if desired. Processing can be accomplished using any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol present.

In one embodiment, the separated and recovered methanol product is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the separated recovered methanol product is sent from the methanol synthesizing unit or vessel to a distillation system. The distillation system contains one or more distillation columns which are used to further separate the desired methanol composition from water and hydrocarbon by-product streams. Desirably, the methanol composition that is separated from the crude methanol comprises a majority of the methanol contained in the methanol product prior to separation.

In one embodiment, the distillation system includes a step of treating the recovered methanol product steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the separated methanol stream from the methanol synthesis reactor by adsorption. In such a system, other components such as fusel oil can be recovered by regenerating the adsorbent.

VI. Use of the Methanol Composition in the Manufacture of Olefins

The methanol product composition of this invention can be used as feed for any conventional process. Examples of such uses include the manufacture of methyl tertiary butyl alcohol (MTBE) for use in reformulated gasolines and oxygenated fuels, the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment, the methanol stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

VII. EXAMPLES

Example 1

Figure 2:
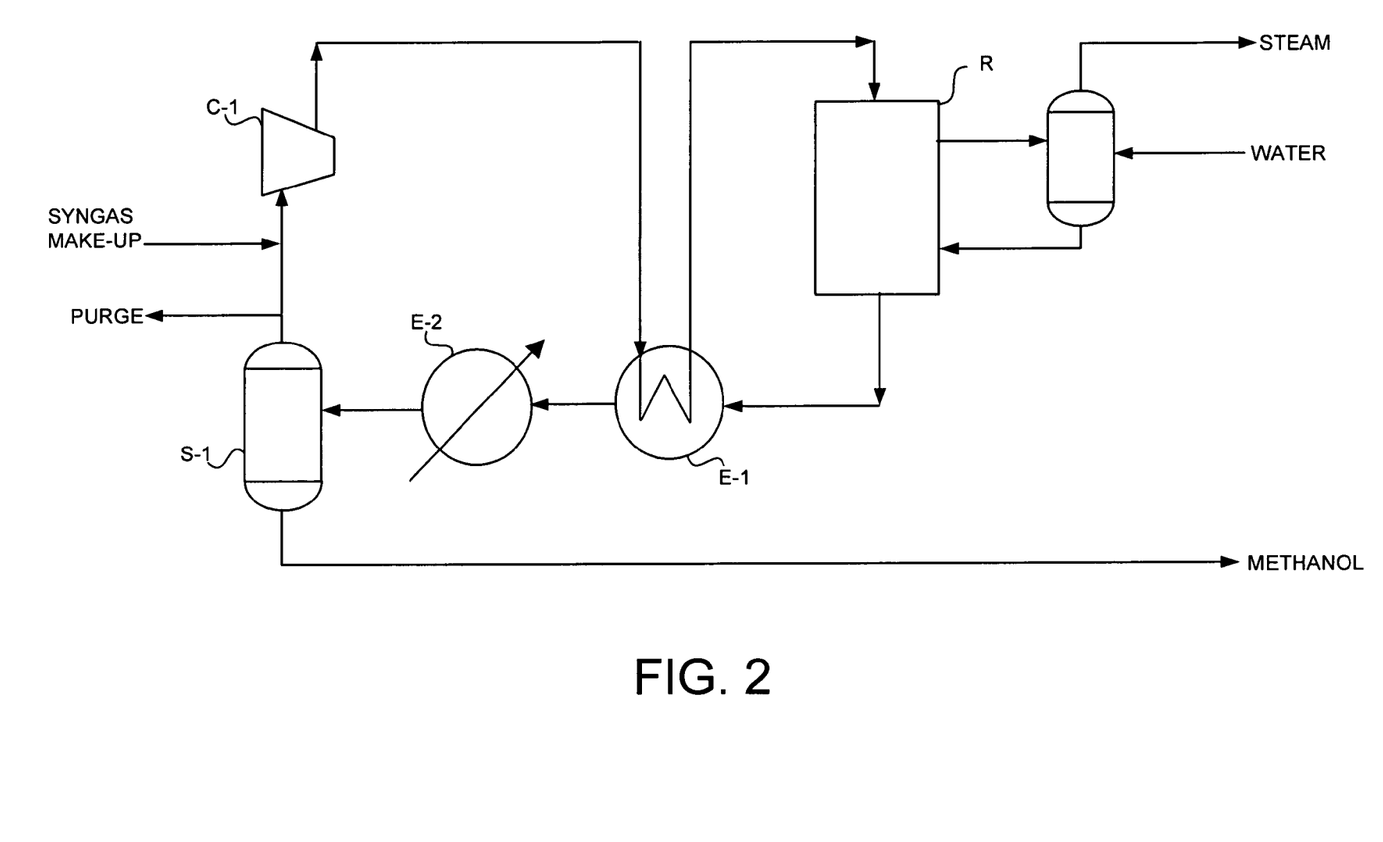
FIG. 2 is a process flow diagram upon which heat and material balances of the examples are based.

A methanol synthesis reaction system is shown in FIG. 2. In accordance with the system in FIG. 2, syngas is sent to a compressor C-1, and the compressed gas is then sent to a heat exchanger E-1 to preheat the compressed syngas. The preheated feed is then sent to a reactor system R, where the syngas components are converted into methanol. In this example, the reactor system is a tubular methanol synthesis reaction system. This reactor system requires internal reactor cooling, and the reactor is kept cool by supplying water, with the water being converted to steam.

Methanol product leaves the reactor system R and is sent to heat exchanger E-1 to preheat the syngas feed. The methanol product is further cooled in heat exchanger E-2, and then sent to separator S-1, where unreacted syngas components are separated from the methanol. A portion of the separated gas components is purged and a portion is added back to the syngas feed and sent to the compressor C-1.

This process was simulated using PRO/II ver. 6.0 software, with a capacity based on 1000 kg-mole/hr of synthesis gas. The corresponding material balance information is shown in Table 1.

TABLE 1

| Steam Description | | Syngas Make-up to C-1 | Syngas from C-1 to E-1 | Syngas from E-1 to R-1 | Product Effluent from R-1 to E-1 | Product from E-1 to E-2 | Purge from S-1 | Methanol from S-1 |
|---|---|---|---|---|---|---|---|---|
| Phase | | Vapor | Vapor | Vapor | Vapor | Mixed | Vapor | Mixed |
| Temperature | (° C.) | 152.6 | 60.4 | 220.0 | 250.0 | 98.2 | 38.0 | 38.0 |
| Pressure | (bar) | 85 | 85 | 85 | 85 | 85 | 85 | 85 |
| Flowrate | (kg-mol/hr) | 999.8 | 499.8 | 499.8 | 4411.5 | 4411.5 | 62.8 | 348.7 |
| Total Mass Rate | (kg/hr) | 11125 | 45499 | 45499 | 45499 | 45499 | 540.5 | 10551 |
| Molar Composition | (%) | | | | | | | |
| Methane | | 1.18 | 11.76 | 11.76 | 13.35 | 13.35 | 14.43 | 0.81 |
| CO | | 25.68 | 10.14 | 10.14 | 5.78 | 5.78 | 6.27 | 0.09 |
| $CO_2$ | | 5.14 | 4.00 | 4.00 | 3.57 | 3.57 | 3.71 | 1.86 |
| $H_2$ | | 67.50 | 69.84 | 69.84 | 64.85 | 64.85 | 70.38 | 0.32 |
| $H_2O$ | | 0.19 | 0.10 | 0.10 | 1.07 | 1.07 | 0.08 | 12.62 |
| $O_2$ | | 0.00 | 0.00 | 0.00 | 0.00 | 0.00 | 0.00 | 0.00 |
| Methanol | | 0.00 | 0.53 | 0.53 | 7.27 | 7.27 | 0.66 | 84.25 |
| $N_2$ | | 0.31 | 3.63 | 3.63 | 4.12 | 4.12 | 4.47 | 0.06 |

The heat transfer duties are as follows:

| E-1 Feed/Effluent Exchanger | 2.54e07 kJ/hr |
| E-2 Final Effluent Cooler | 1.84e07 kJ/hr |
| R Tubular Methanol Synthesis Reactor | 2.28e07 kJ/hr |

The heat transfer surface area for exchangers E-1 and E-2 can be estimated assuming a heat transfer coefficient of 428 J $m^{-2}$ $s^{-1}$° $K^{-1}$ (75 Btu $hr^{-1}$ $ft^{-2}$° $F.^{-1}$) and using the temperatures shown in Table 1 (Coolant temperature for E-2 assumed to be 30° C.). The resulting surface area is 488 $m^2$ for E-1 and 474 $m^2$ for E-2.

The reactor can be sized based on process conditions at the reactor exit and on the following assumptions:

| Axial pressure drop | 22.3 kPa $m^{-1}$ (1.0 psi $ft^{-1}$) |
| Catalyst particle diameter | 5 mm |
| Catalyst bulk density | 1100 kg $m^{-3}$ |
| Catalyst particle density | 2000 kg $m^{-3}$ |
| Gas Density | 19.3 kg $m^{-3}$ |
| Gas viscosity | 2.0e−05 kg $m^{-1}$ $s^{-1}$ |
| Tube diameter | 0.0254 m (1 inch) |
| Tube spacing and pitch | 1.25" triangular |

Based on this tube geometry, 44% of the cross sectional area of the reactor contains catalyst and the outside specific surface area is 91.3 m²/m³. The reactor diameter that meets the axial pressure drop criteria is 1.62 m.

The catalyst volume required can be calculated from the following kinetic model (Szarawara, J. and Reychman, K., 1980. *Int. Chem. Proc.*, 1: 331):

$$CO + 2H_2 \leftrightarrow CH_3OH \quad (1)$$

$$CO_2 + 3H_2 \leftrightarrow CH_3OH + H_2O \quad (2)$$

$$r_1 = 0.2032 \exp\left(\frac{-2954}{T}\right) p_{CO}^{0.5} p_{H2} \left(1 - \frac{p_{CH3OH}}{K_1 p_{CO} p_{H2}^2}\right) \quad (3)$$

$$r_1 = 8.893 \times 10^{-3} \exp\left(\frac{-6163}{T}\right) p_{CO2}^{0.5} p_{H2}^{1.5} \left(1 - \frac{p_{CH3OH}}{K_2 p_{CO2} p_{H2}^3}\right) \quad (4)$$

where the reaction rates are in kg-mol $kg_{cat}^{-1} h^{-1}$, the partial pressures are in bar, the temperature is in °K, and $K_1$ and $K_2$ are the equilibrium constants for reactions (1) and (2).

Integration of these rate expressions at a constant 250° C. temperature for a plug flow reactor yields a catalyst requirement of 3044 kg, or a volume 2.77 m³. This requires a reactor tube length of 3.04 m. The heat transfer surface area contained within this reactor is 575 m².

Example 2

In this example, the reactor system R of FIG. 2 is a dense fluid bed synthesis reactor in which the catalyst in the dense bed is maintained at a solids volume fraction of from 0.35 to 0.45. In this configuration, the hot reactor effluent stream from the reactor is used to generate low pressure (1.7 bar) steam in an external heat exchanger (not shown) within the reactor system R. Warm reactor effluent leaving the heat exchanger is used to preheat the reactor feed in exchanger E-1. The reaction temperature is controlled by controlling the amount of feed preheat in E-1. The material balance is shown in Table 2.

The heat transfer duties are as follows:

| | |
|---|---|
| External waste heat boiler to R | 1.91e07 kJ/hr |
| E-1 Feed/Effluent Exchanger | 0.26e07 kJ/hr |
| E-2 Final Effluent Cooler | 2.21e07 kJ/hr |

Using the same assumptions for the heat exchangers as in Example 1, the following surface areas are calculated:

| | |
|---|---|
| External waste heat boiler to R | 249 m² |
| E-1 Feed/Effluent Exchanger | 35.5 m² |
| E-2 Final Effluent Cooler | 514 m² |

The reactor diameter is sized based on the desired gas superficial velocity. A velocity of 1 m/sec was selected to achieve turbulent fluidization with good gas-solid contacting and high internal solid circulation to achieve a high degree of gas backmixing. These properties achieve isothermal operation with constant gas composition throughout the reaction zone. The reactor diameter required for 1 m/sec superficial gas velocity is 0.92 m.

The same kinetic model of Example 1 is used to determine the catalyst volume required. Due to the gas backmixing, the average reactant concentrations are lower in the backmixed case compared to the plug flow case. A larger catalyst weight of 3875 kg is required for the fluid bed case. At the superficial velocity of 1 m/sec, the solids fraction in the dense portion of the fluid bed is about 0.4. The calculated height of catalyst in the dense portion of the bed is 7.24 m. The height of the "freeboard" section of the bed is determined by the cyclone pressure drop and other factors, and is typically about 15 m, for an overall height of 22.2 m.

The data from Example 1 and Example 2 are summarized and shown in Table 3.

TABLE 2

| Steam Description | | Syngas Make-up to C-1 | Syngas from C-1 to E-1 | Recycle Syngas from S-1 to C-1 | Purge from S-1 | Methanol from S-1 | Syngas from E-1 to R | Product from R to E-1 | Product from E-1 to E-2 |
|---|---|---|---|---|---|---|---|---|---|
| Phase | | Vapor | Vapor | Vapor | Vapor | Mixed | Vapor | Vapor | Vapor |
| Temperature | (° C.) | 152.6 | 60.3 | 38.0 | 38.0 | 38.0 | 77.0 | 107.5 | 125.0 |
| Pressure | (bar) | 85 | 85 | 85 | 85 | 85 | 85 | 85 | 85 |
| Flowrate | (kg-mol/hr) | 999.8 | 5000 | 4000 | 60 | 350 | 5000 | 4410 | 4410 |
| Total Mass Rate | (kg/hr) | 11125 | 46499 | 35295 | 533 | 10590 | 46499 | 46418 | 46418 |
| Molar Composition | (%) | | | | | | | | |
| Methane | | 1.18 | 12.05 | 14.74 | 14.74 | 0.83 | 12.05 | 13.63 | 13.63 |
| CO | | 25.68 | 10.31 | 6.46 | 6.46 | 0.09 | 10.31 | 5.96 | 5.96 |
| CO$_2$ | | 5.14 | 4.14 | 3.89 | 3.89 | 1.94 | 4.14 | 3.73 | 3.73 |
| H$_2$ | | 67.50 | 69.03 | 69.49 | 69.49 | 0.32 | 69.03 | 64.00 | 64.00 |
| H$_2$O | | 0.19 | 0.10 | 0.08 | 0.08 | 12.61 | 0.10 | 1.07 | 1.07 |
| O$_2$ | | 0.00 | 0.00 | 0.00 | 0.00 | 0.00 | 0.00 | 0.00 | 0.00 |
| Methanol | | 0.00 | 0.53 | 0.67 | 0.67 | 84.15 | 0.53 | 7.29 | 7.29 |
| N$_2$ | | 0.31 | 3.84 | 4.68 | 4.68 | 0.06 | 3.84 | 4.31 | 4.31 |

TABLE 3

|  | Example 1 | Example 2 |
|---|---|---|
| Steam generated from R |  |  |
| Duty, kJ/hr | 2.28e07 | 1.91e07 |
| Surface area, $m^2$ | 575 | 249 |
| Feed/Effluent Exchange E-1 |  |  |
| Duty, kJ/hr | 2.54e07 | 0.26e07 |
| Surface area, $m^2$ | 488 | 36 |
| Final cooler E-2 |  |  |
| Duty, kJ/hr | 2.28e07 | 2.21e07 |
| Surface area, $m^2$ | 474 | 514 |
| TOTAL EXCHANGER SURFACE, $m^2$ | 1537 | 799 |
| Reactor Type | Tubular | Dense Fluid Bed |
| Diameter, m | 1.62 | 0.92 |
| Height of reaction zone, m | 3.04 | 7.24 |
| Volume of reaction zone, $m^3$ | 6.27 | 4.81 |
| Total reactor height, m | 3.04 | 22.2 |
| Total reactor volume, $m^3$ | 6.27 | 14.8 |
| Number of 1" diameter tubes | 2360 | 0 |

Example 3

In this example, the reactor system R of FIG. 2 is a fast fluid bed reactor. The fast fluid bed reactor operates at a higher gas velocity than the reactor of Example 2, and achieves a closer approach to plug flow behavior than the reactor of Example 2. The solids recovered from the disengaging zone and cyclone are returned to the reactor, resulting in a high circulation rate of solids. The thermal mass of the solids contributes to a relatively small temperature difference across the fast fluid bed reactor.

The heat and material balance for this example is identical to that of Example 2 (dense bed reactor), including total exchanger surface. The approach to plug flow behavior of the gas in the fast flow regime requires a smaller catalyst volume for a given conversion than a reactor with gas backmixing as in a dense bed reactor. However, the higher gas velocity in the fast fluid reactor makes the catalyst more dilute, increasing the overall volume of the reaction zone. Table 4 compares the reactor velocities, catalyst concentrations, and reactor volumes for Examples 1-3. The overall reactor volume for the fast fluid reactor of this example is highest, although the reactor diameter is smallest. The small diameter of the riser can offer cost advantages under some circumstances, even though the height and total reactor volume are greater.

TABLE 4

|  | Tubular Reactor | Dense Fluid Bed Reactor | Fast Fluid Bed Reactor |
|---|---|---|---|
| Diameter, m | 1.62 | 0.92 | 0.50 |
| Superficial gas velocity, $m \cdot s^{-1}$ | 0.3 | 1.0 | 3.4 |
| Catalyst volume required, $m^3$ | 3044 | 3875 | 3044 |
| Average catalyst particle diameter, microns | 5000 | 80 | 80 |
| Volume fraction solid in reaction zone | 0.58 | 0.4 | 0.18 |
| Height of reaction zone, m | 3.04 | 7.24 | 42.6 |
| Volume of reaction zone, $m^3$ | 6.27 | 4.81 | 8.37 |
| Diameter of disengaging zone, m | N/A | 0.92 | 1.3 |
| Height of disengaging zone, m | N/A | 15 | 10 |
| Volume of disengaging zone, $m^3$ | N/A | 10.0 | 13.4 |
| Total reactor volume, $m^3$ | 6.27 | 14.8 | 21.8 |
| Number of 1" diameter tubes | 2360 | 0 | 0 |

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A process for making methanol product in a fluid bed reactor, comprising:
   flowing a gas containing carbon monoxide and hydrogen through a fluidized bed zone of a fluid bed reactor at a superficial gas velocity of from 2 to 20 meters per second;
   contacting the gas with methanol synthesis catalyst in the fluidized bed zone to form the methanol product, wherein the fluidized bed zone is maintained at a solids volume fraction of from 0.05 to 0.35; and
   separating the catalyst from the methanol product in an upper portion of the fluid bed reactor.

2. The process of claim 1, wherein the fluidized zone is maintained at a solids volume fraction of from 0.07 to 0.3.

3. The process of claim 2, wherein the fluidized zone is maintained at a solids volume fraction of from 0.1 to 0.25.

4. The process of claim 1, wherein the catalyst has a particle size of from 20 to 300 microns.

5. The process of claim 1, wherein the fluid bed reactor has an internal heat exchange surface area ($m^2$) relative to internal reactor volume ($m^3$) of not greater than 100 $m^2/m^3$.

6. The process of claim 1, wherein the fluidized bed zone portion of the fluid bed reactor has a reactor height to diameter ratio of at least 2.

7. The process of claim 1, wherein the process includes one or more reactors with no two reactors in series.

8. The process of claim 1, wherein the catalyst that is separated from the methanol product is returned to the fluidized bed reactor.

9. The process of claim 1, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

10. The process of claim 1, wherein the fluidized bed zone is maintained at a temperature of from 150° C. to 350° C.

11. The process of claim 1, wherein the gas flowing through the fluidized bed zone flows into the fluidized bed zone at a temperature of from 50° C. to 150° C.

12. The process of claim 1, wherein the gas flowing through the fluidized bed zone further contains $CO_2$, and the gas is contacted with the catalyst at a rate to control molar conversion of the CO and $CO_2$, based on the total amount of CO and $CO_2$ in the feed, in a range of from 20% to 70%.

13. The process of claim 1, further comprising contacting at least a portion of the methanol product with an olefin forming catalyst to form an olefin product.

14. A process for making methanol product in a fluid bed reactor, comprising:
   contacting a gas containing carbon monoxide and hydrogen with methanol synthesis catalyst in a fluidized bed zone of a fluid bed reactor at a superficial gas velocity of from 2 to 20 meters per second to form the methanol product, wherein the fluidized bed zone is maintained at a solids volume fraction of from 0.05 to 0.35;
   separating the catalyst from the methanol product in an upper portion of the fluid bed reactor; and
   returning the catalyst that is separated from the methanol product to the fluidized bed zone of the fluid bed reactor.

15. The process of claim 14, wherein the fluidized bed zone is maintained at a solids volume fraction of from 0.07 to 0.3.

16. The process of claim 15, wherein the fluidized bed zone is maintained at a solids volume fraction of from 0.1 to 0.25.

17. The process of claim 14, wherein the catalyst has a particle size of from 20 to 300 microns.

18. The process of claim 14, wherein the fluid bed reactor has an internal heat exchange surface area ($m^2$) relative to internal reactor volume ($m^3$) of not greater than 100 $m^2/m^3$.

19. The process of claim 14, wherein the fluidized bed zone portion of the fluid bed reactor has a reactor height to diameter ratio of at least 2.

20. The process of claim 14, wherein the process includes one or more reactors with no two reactors in series.

21. The process of claim 14, wherein the catalyst that is separated from the methanol product is returned to the fluidized bed reactor.

22. The process of claim 14, wherein the methanol synthesis catalyst includes an oxide of at least one element selected from the group consisting of copper, silver, zinc, boron, magnesium, aluminum, vanadium, chromium, manganese, gallium, palladium, osmium and zirconium.

23. The process of claim 14, wherein the fluidized bed zone is maintained at a temperature of from 150° C. to 350° C.

24. The process of claim 14, wherein the gas flows into the fluid bed zone at a temperature of from 50° C. to 150° C.

25. The process of claim 14, wherein the gas further contains $CO_2$, and the gas is contacted with the catalyst at a rate to control molar conversion of the CO and $CO_2$, based on the total amount of CO and $CO_2$ in the feed, in a range of from 20% to 70%.

26. The process of claim 14, further comprising contacting at least a portion of the methanol product with an olefin forming catalyst to form an olefin product.

* * * * *